(12) United States Patent
Chornenky

(10) Patent No.: US 6,810,109 B2
(45) Date of Patent: Oct. 26, 2004

(54) X-RAY EMITTING SYSTEM AND METHOD

(75) Inventor: Victor Chornenky, Santa Rosa, CA (US)

(73) Assignee: Medtronic Ave, Inc., Santa Rosa, CA (US)

(*) Notice: Subject to any disclaimer, the term of this patent is extended or adjusted under 35 U.S.C. 154(b) by 0 days.

(21) Appl. No.: 09/905,267

(22) Filed: Jul. 13, 2001

(65) Prior Publication Data

US 2003/0012340 A1 Jan. 16, 2003

(51) Int. Cl.[7] .................................................. H05G 1/44
(52) U.S. Cl. ........................ 378/108; 378/110; 378/112
(58) Field of Search ................................ 378/122, 101, 378/108, 109, 110, 111, 112, 65, 97

(56) References Cited

U.S. PATENT DOCUMENTS 4,797,905 A * 1/1989 Ochmann et al. ........... 378/108
6,069,938 A * 5/2000 Chornenky et al. ......... 378/122
6,249,565 B1 * 6/2001 Tarr ............................ 378/65

* cited by examiner

Primary Examiner—David V. Bruce
Assistant Examiner—Elizabeth Keaney

(57) ABSTRACT

An x-ray emitting system and method for administering a predetermined x-ray dose rate are provided. The system includes an x-ray emitter, a controller operably connected to the x-ray emitter, a current sensor operably connected to the controller, and a voltage sensor operably connected to the controller. The controller determines an actual dose rate based on a received current sensor signal and a received voltage sensor signal and adjusts a supplied voltage to allow the actual dose rate to match a predetermined dose rate. The method of operating a device for emitting x-rays includes: applying a voltage from a voltage source to the device, measuring current and voltage within the device, determining an actual dose rate based on the measured current and voltage, comparing a desired dose rate to the actual dose rate, adjusting the applied voltage, and matching the actual dose rate to the desired dose rate.

20 Claims, 2 Drawing Sheets

X-RAY EMITTING SYSTEM AND METHOD

TECHNICAL FIELD OF THE INVENTION

The present invention relates to a system and method for emitting x-rays, and more specifically, the invention relates to a system and method for administering a desired x-ray dose from an x-ray device.

BACKGROUND OF THE INVENTION

X-ray emitters such as x-ray catheters typically consist of an anode and cathode assembly mounted in a miniature vacuum tube. During operation, a high DC voltage (15 to 35 kV) is applied to the assembly from a power source. A high electrical field in the anode-to-cathode gaps causes an electron field emission from the cathode surface. The electrons, emitted into the vacuum gap, are accelerated by the electrical field and strike the anode, radiating x-ray energy as they are stopped.

The emission properties of a thermionic cathode, or hot cathode, depend on the temperature of the cathode surface. A hot cathode utilizes an additional electrode providing a low voltage current for heating the cathode surface. The emission properties and the current at the anode are improved by elevating the cathode surface temperature. Furthermore, the anode current and voltage can be controlled and stabilized independently from each other.

A field emission cathode, or cold cathode, is sometimes favored to a hot cathode in medical procedures and other applications. The cold cathode provides a smaller size and lower operating temperature due to the lack of the heating electrode. In a cold cathode, the value of the field emission current is exponential function of the applied voltage. Therefore, the cold cathode cannot provide independent control of the voltage and current.

X-ray catheters are utilized during medical procedures including percutaneous transluminal coronary angioplasty (PTCA) and when irradiation of vessels or body cavities is required. The successful operation of the x-ray catheter requires the ability to administer a precise radiation dose to a target area. The inherent instability of electron emission from cold cathodes provides a technical difficulty in designing power supplies for the catheters. Ideally, the voltage and current should be measured so that the irradiation dose can be calculated in real-time. The calculated dose could then be adjusted to correspond to a desired dose for the given application.

At least two strategies exist for measuring and controlling the irradiation dose emitted from x-ray devices including field emission cathodes. One method monitors and integrates current while voltage is stabilized. The total accumulated dose is calculated as proportional to the electric charge passed through the emitter. A narrow set of stabilized operating voltages (18 to 21 kV), however, is required to maintain the irradiation rate at a nominal value.

Another method utilizes high voltage pulses with stabilized amplitude. The U.S. Pat. No. 6,069,938 issued May 30, 2000 to Chornenky et al. is an example of a method and x-ray device using a pulse high voltage source. In the Chornenky patent, current passing through the x-ray emitter is measured and integrated. Rectangular voltage pulses with stabilized amplitude and known cycle are applied to the emitter. The average electrical current is stabilized by changing the width of the pulses, thus stabilizing the irradiation rate and controlling dose. The technical difficulty of switching high voltage power up and down is not desirable from a manufacturing and cost viewpoint.

The disclosed and other strategies may provide a stable and controlled irradiation dose rate. The current designs, however, have limitations including large unit size and cost, heat generation, and narrow operating voltage range. Therefore, it would be desirable to achieve an x-ray device with a stabilized irradiation rate that overcomes the aforementioned and other disadvantages.

SUMMARY OF THE INVENTION

One aspect of the invention provides a system for emitting x-rays comprising: an x-ray emitter, a controller operably connected to the x-ray emitter, a current sensor operably connected to the controller, and a voltage sensor operably connected to the controller. The controller may determine an actual dose rate based on a received current sensor signal and a received voltage sensor signal and may adjust a supplied voltage to allow the actual dose rate to match a predetermined dose rate. The current and voltage sensors measure the current and voltage, respectively, through the x-ray emitter a plurality of times per second. The controller may adjust the actual dose rate based on an irradiation depth by correcting for tissue radiation absorption and an increased radial target area with increasing treatment radius. The controller may further comprise a current integrator operably connected to the current sensor and the controller to integrate instant current values over time to determine an accumulated charge. The actual dose rate may be calculated a plurality of times per second and may be determined according to: $D = f \times I \times (V - V_0)^2$ wherein D is the actual dose rate at a distance r from the emitter, f is a constant, I is a current through the x-ray emitter, V is a voltage applied across an anode and a cathode, and $V_0$ is a constant.

Another aspect of the invention provides for a method of operating a device for emitting x-rays comprising: applying a voltage from a voltage source to the device, measuring current and voltage within the device, determining an actual dose rate based on the measured current and voltage, comparing a desired dose rate to the actual dose rate, adjusting the applied voltage, and matching the actual dose rate to the desired dose rate. The adjusting of the applied voltage may comprise stabilizing the actual dose rate; an operator may select the desired dose rate.

Yet another aspect of the invention provides for a computer usable medium storing a program for: determining an actual dose rate based on the measured current and voltage, comparing a desired dose rate to the actual dose rate, adjusting the applied voltage, and matching the actual dose rate to the desired dose rate.

The foregoing and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Figure 1:
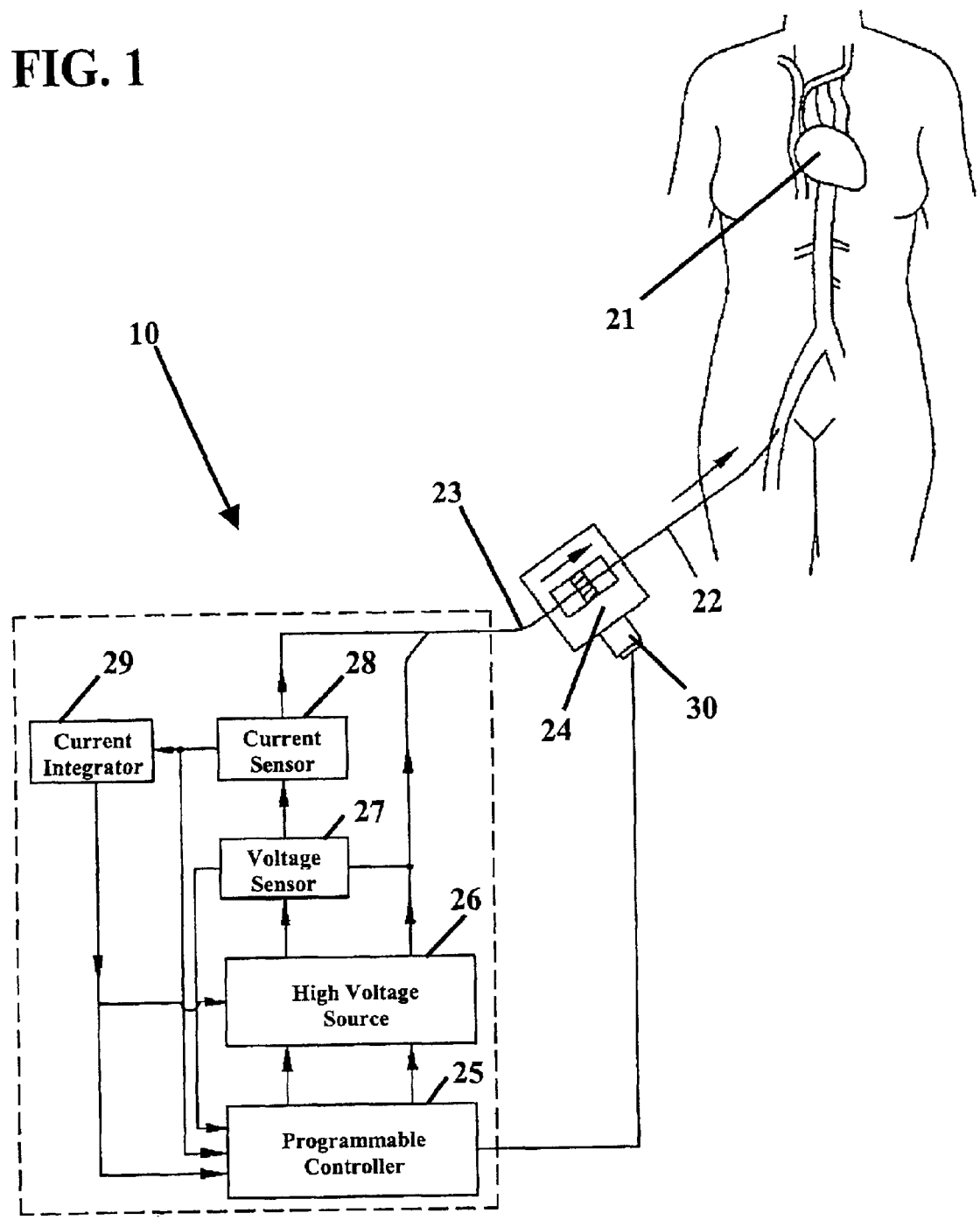
FIG. 1 is a schematic overview of one embodiment of the present invention.

A schematic overview of one embodiment of the invention is shown in FIG. 1. The x-ray system 10 comprises: an x-ray emitter 21, a programmable controller 25 operably connected to the x-ray emitter 21, a current sensor 28 operably connected to the programmable controller 25, and a voltage sensor 27 operably connected to the programmable controller 25.

Another embodiment of the invention provides for a method of operating a device for emitting x-rays, such as an x-ray emitter 21, comprising: applying a voltage from a voltage source to the device, measuring current and voltage within the device, determining an actual dose rate based on the measured current and voltage, comparing a desired dose rate to the actual dose rate, adjusting the applied voltage, and matching the actual dose rate to the desired dose rate. The configuration and operation of the aforementioned system and method may be further understood by the following description of the use of the embodiment.

The x-ray emitter 21 of the present invention may be a field emission diode including an anode and a cathode arranged within a vacuum housing to produce x-ray radiation. The cathode may include a thin diamond film, and may include a getter material that is activated to improve the quality of the vacuum within the housing, as described is U.S. patent application Ser. No. 08/806,244, which is incorporated by reference herein. Examples of suitable x-ray emitters of this application, components of the emitter, and various delivery systems for positioning such a catheter in a passage within a patient's body have been described in other patents. X-ray emitters are disclosed in U.S. Pat. No. 6,108,402 issued Aug. 22, 2000 to Chornenky and U.S. Pat. No. 6,095,966 issued to Chornenky et al. and are incorporated by reference herein. Several examples of delivery devices, systems and methods that may be used with an x-ray emitter are described in U.S. Pat. No. 6,210,312 issued Apr. 3, 2001 to Nagy and U.S. Pat. No. 6,183,410 issued Feb. 6, 2001 to Jacobsen et al., and are incorporated by reference herein.

The x-ray emitter 21 is schematically shown in FIG. 1 at a position inside a patient's body. One skilled in the art can recognize that the x-ray emitter 21 may be utilized in a wide spectrum of medical and technical applications and is not limited to use in a human body. The x-ray emitter 21 may be connected to the programmable controller 25 via a cable 23 and situated within a sheath 22 lumen. The x-ray emitter 21 and cable 23 may be inserted into the patient's body via a suitable blood vessel and advanced through the vessel to the desired treatment area.

The voltage sensor 27 and the current sensor 28 may be connected to the high voltage power source 26 and the cable 23. The cable 23 may be connected to a high voltage power source 26. Those skilled in the art will appreciate that many different high voltage power sources may be used with the present invention. In one embodiment, the high voltage power source 26 supplies a voltage ranging from about 15 to 35 kV and current ranging from about 10 to 100 microamperes to the x-ray emitter 21. The voltage sensor 27 may be used to measure a voltage through the x-ray emitter 21 a plurality of times per second. The current sensor 28 may be used to measure a current through the x-ray emitter 21 a plurality of times per second. Many well-known voltage and current sensors may be used with this embodiment. For example, a voltmeter may be used to measure the voltage and an amperemeter may be used to measure the current. In one embodiment, the voltage sensor 27 and the current sensor 28 may perform their respective measurements about every 10 to 100 milliseconds. Additionally, the x-ray system 10 and method may include a current integrator 29 operably connected to the current sensor 28 and the programmable controller 25 to integrate instant current values over time to determine an accumulated charge.

The x-ray system 10 and method may further include a catheter pull-back assembly 24. The catheter pull-back assembly 24 may include a body with a carriage slidably mounted on it. The sheath 22 may be connected to the body and the cable 23 may be connected to the carriage. By sliding the carriage on the body of the catheter pull-back assembly 24, the cable 23 may be retracted within the sheath 22, thereby moving the x-ray emitter 21. The catheter pull-back assembly 24 may further include means for actuating the carriage from a distance. For example, an actuating cable may be connected to the carriage so that the carriage can be actuated by a control means, such as electro motor 30 separate from the catheter pull-back assembly 24. The catheter movement may also be controlled by hand.

The programmable controller 25 may be connected to the high voltage power source 26 and ultimately may determine the supplied voltage to the x-ray emitter 21. The programmable controller 25 may include different configurations of microprocessor(s), circuit board(s), component(s), and input and output devices depending on the particular intended use of the invention. The programmable controller 25 may run an algorithm in the form of a computer program to control components of the x-ray system 10 and method including the high voltage power source 26. The computer program may determine an actual dose rate based on the measured current and voltage, compare a desired dose rate to the actual dose rate, adjust the applied voltage, and match the actual dose rate to the desired dose rate.

The programmable controller 25 may be connected to the voltage sensor 27 and the current sensor 28 and may be connected to the current integrator 29 and the catheter pull-back assembly 24. In one embodiment, an electrical or digital connection may be made between the device and the programmable controller 25 to provide for a sharing of measurements. In one embodiment, a mechanical connection, such as an actuator cable from the catheter pull-back assembly 24 to the programmable controller 25, may be made to control movement of the x-ray emitter 21 via the catheter pull-back assembly 24.

The programmable controller 25 may determine an actual x-ray dose rate based on a received current sensor 28 signal and a received voltage sensor 27 signal. The programmable controller 25 may adjust a supplied voltage to allow the actual dose rate to match a predetermined dose rate. Alternatively, the programmable controller 25 may determine the actual dose rate based on received current integrator 29 information, for example, the accumulated charge. The programmable controller 25 may adjust the actual dose rate based on an irradiation depth by correcting for tissue radiation absorption and an increased radial target area with increasing treatment radius. An operator, such as a physician performing the x-ray irradiation procedure, may select the predetermined dose rate and a total predetermined dose.

In one embodiment, the actual dose rate may be calculated based on a formula: $D = f \times I \times (V - V_0)^2$ wherein D is the actual dose rate at an irradiation depth, r, from the x-ray emitter 21, f is a constant independent of current or voltage, I is a current through the x-ray emitter 21, V is a voltage applied across an anode and a cathode, and $V_0$ is a constant. The constant, f, describes the absorption of x-ray radiation and the spread of the radiation over a larger cylindrical target area as the depth into tissue increases. In one embodiment, the constant, f, depends only on the irradiation depth, r. The irradiation depth, r, may depend on vessel wall x-ray absorption and increased radial target area with increasing treatment radius. The actual dose rate may be calculated or measured experimentally and tabulated. This tabulation, for example, may provide an operator of the x-ray system 10 with the dose rate for given values of the current, I, voltage, V, and irradiation depth, r. $V_0$ is a constant that depends on the design of the x-ray emitter 21 and represents a cut-off energy of the x-ray radiation that is filtered out by the emitter shell and, thus, does not reach the target area. The programmable controller 25 may adjust the actual dose rate based on the irradiation depth, r, and the cut-off energy, $V_0$, determined by the spectrum of the emitted radiation. Theoretical simulations have shown that for Bremsstrahlung radiation the dose rate at the irradiation depth, r, from the x-ray emitter 21 can be described using the formula. For any x-ray emitter, the values, f and $V_0$, vary somewhat depending on the actual thickness of the emitter wall and the metal coating on the outside surface of the emitter. In one embodiment, a practical and precise way to measure the values, f and $V_0$, involves measuring the actual dose rate, D, at several different operating voltages. A curve fitting algorithm is then applies the data points to the formula $D=f \times I \times (V-V_0)^2$ to experimentally determine f and $V_0$.

Figure 2:
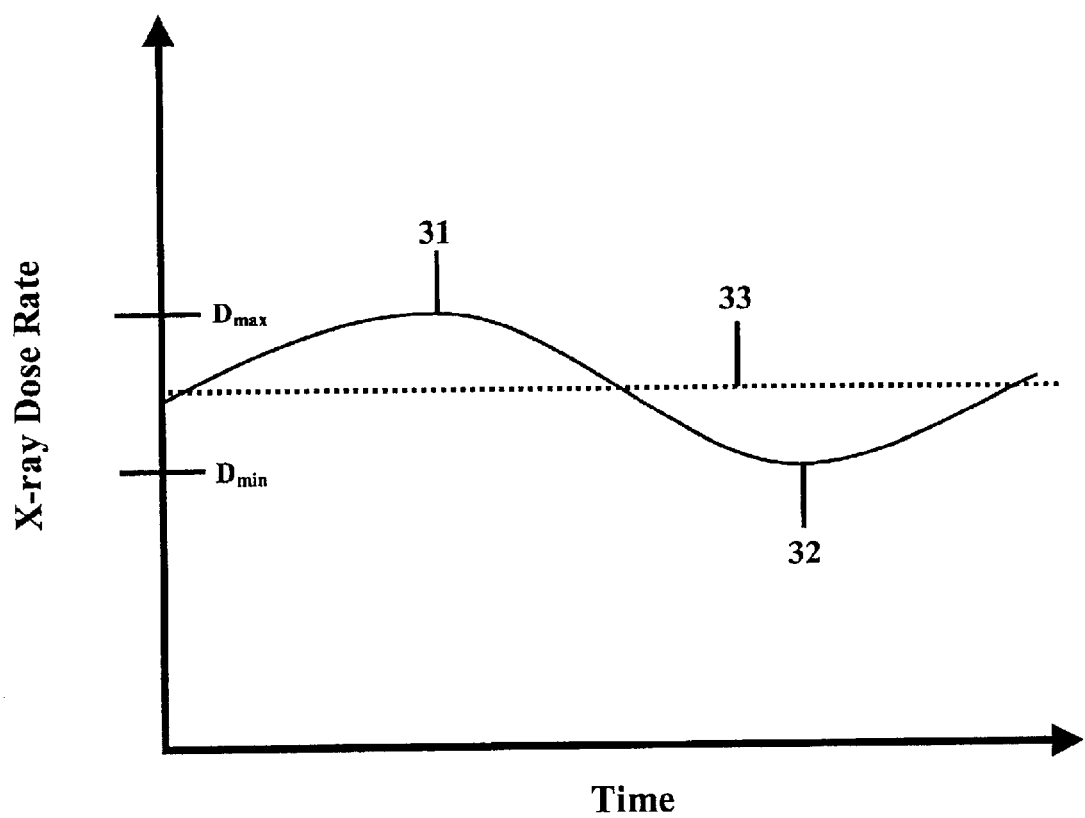
FIG. 2 is a schematic diagram showing an actual dose rate as a function of time in another embodiment of the present invention.

The actual dose rate may be calculated a plurality of times per second. Ideally, the programmable controller 25 may perform the calculation about every 10 to 100 milliseconds. The calculation may involve utilizing information from the current sensor 28, the current integrator 29, the voltage sensor 27, or combinations thereof. Furthermore, those skilled in the art will appreciate that any number of alternative formulae or approximative methods may effectively utilize the sensor(s) signal information to determine the actual dose rate. The programmable controller 25 then compares the calculated actual dose rate to the predetermined dose rate and adjusts the applied voltage to the x-ray emitter 21 thereby stabilizing the actual dose rate. For example, if the actual dose rate is above the predetermined dose rate, the voltage provided to the x-ray emitter 21 is lowered accordingly to match the actual dose rate to the predetermined dose rate. The process is shown in FIG. 2. Instabilities of the actual dose rate that may result in actual dose rate maxima 31, $D_{max}$, and minima 32, $D_{min}$, are balanced by the programmable controller. As a result, a mean value of the actual dose rate approximately matches the predetermined dose rate 33 and a stabilized dose rate is achieved. Furthermore, the use of both current and voltage values to approximate the actual dose rate may provide an ability to administer a precise total radiation dose to a target area and may overcome an inherent instability of electron emission from cold cathodes.

In one embodiment, the x-ray emitter 21 may be positioned in a passage in a patient's body according to known procedures for catheterization. The x-ray emitter 21 may be positioned near a particular area that is to be treated with radiation. For example, the x-ray emitter 21 may be positioned near a particular treatment area such that it may be successively withdrawn during the treatment to deliver radiation to the entire treatment area. The x-ray emitter 21 may be delivered by connecting to the cable 23 and advancing the cable 23 through the sheath 22 that has been introduced into the passage. Furthermore, the sheath 22 may be advanced into the passage using a guide wire (not shown) by first introducing the guide wire into the passage and then advancing the sheath 22 along the guide wire.

X-ray radiation in the range of about 10 to 50 Grays may be applied to an area of the interior of a passage during treatment, for example, to prevent restenosis. Preferably, x-ray radiation in the range of 15 to 30 Grays may be applied to an interior body site. The treatment may be structured to last about 2 to 10 minutes. In one embodiment, the treatment may be structured to last about 3 to 5 minutes. The x-ray emitter 21 may be repositioned during the treatment course, depending on the length of the area requiring treatment.

In one embodiment, any particular treatment parameters for the patient may be entered into the programmable controller 25. For example, the operating voltage, the length of the treatment area, and the desired dose rate may be entered as treatment parameters. The operating voltage determines the depth of x-ray penetration. The actual dose rate may depend on the surrounding tissue and the medical condition to be treated. When the x-ray emitter 21 is in its initial position and the treatment parameters have been entered the treatment may begin. High voltage may be supplied to the x-ray emitter and x-ray radiation is emitted. Once a total actual dose administered matches a total desired dose, the programmable controller 25 may stop the supply of high voltage to the x-ray emitter 21. The x-ray emitter 21 and sheath 22 may be removed from the patient to conclude treatment.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A system for emitting x-rays comprising:

an x-ray emitter;

a controller operably connected to the x-ray emitter;

a current sensor operably connected to the controller; and a voltage sensor operably connected to the controller wherein the controller determines an actual dose rate based on an emitter cut-off energy, a radiation depth, and received current and voltage, sensor signals, and adjusts an applied voltage to allow the actual dose rate to match a predetermined dose rate; wherein the applied voltage is increased when the actual dose rate is less thin the predetermined dose rate, and the applied voltage is decreased when the actual dose rate is greater than the predetermined dose rate.

2. The system of claim 1 wherein the current sensor measures the current through the x-ray emitter a plurality of times per second.

3. The system of claim 1 wherein the voltage sensor measures the voltage through the x-ray emitter a plurality of times per second.

4. The system of claim 1 wherein the controller adjusts the actual dose rate based on an irradiation depth.

5. The system of claim 1 wherein the actual dose rate is calculated a plurality of times per second.

6. The system of claim 1 wherein the actual dose rate is determined according to:

$D=f \times I \times (V-V_0)^2$; wherein

D=the actual dose rate at a distance r from the emitter, f=a constant,

I=a current through the x-ray emitter,

V=a voltage applied across an anode and a cathode, and $V_0$=a constant.

7. The system of claim 1 wherein the controller adjusts the actual dose rate by correcting for tissue radiation absorption.

8. The system of claim 1 wherein the controller adjusts the actual dose rate by correcting for an increased target area with an increasing treatment radius.

9. The system of claim 1 further comprising a current integrator operably connected to the current sensor and the controller to integrate instant current values over time to determine an accumulated charge.

10. A method of operating a device for emitting x-rays comprising:
    applying a voltage from a voltage source to the device;
    measuring current and voltage within the device;
    determining an actual dose rate based on an emitter cut-off energy, a radiation depth, and the measured current and voltage;
    comparing a desired dose rate to the actual dose rate;
    increasing the applied voltage when the actual dose rate is less than the predetermined dose rate; and
    decreasing the applied voltage when the actual dose rate is greater than the predetermined dose rate.

11. The method of claim 10 wherein the measuring of the current and voltage comprises sampling the current and voltage a plurality of times per second.

12. The method of claim 10 wherein the determining of the actual dose rare comprises adjusting for an irradiation depth.

13. The method of claim 10 wherein the determining of the actual dose rate comprises correcting for tissue radiation absorption.

14. The method of claim 10 wherein the determining of the actual dose rate comprises calculating the actual dose rate a plurality of times per second.

15. The method of claim 10 wherein the determining of the actual dose rate comprises calculating the actual dose rate according to:
    $D = f \times I \times (V-V_0)^2$; wherein
    D=the actual dose rate at a distance r from the emitter.
    f=a constant,
    I=a current through the x-ray emitter.
    V=a voltage applied across an anode and a cathode, and
    $V_0$=a constant.

16. The system of claim 10 wherein the determining of the actual dose rate comprises integrating instant current values over time to determine an accumulated charge.

17. The method of claim 10 wherein the adjusting of the applied voltage comprises stabilizing the actual dose rate.

18. The method of claim 10 further comprising selecting the desired dose rate by an operator.

19. A computer usable medium storing a program comprising;
    computer readable code for applying a voltage from a voltage source to the device;
    computer readable code for measuring current and voltage within the device;
    computer readable code for determining an actual dose rate based on an emitter cut off energy, a radiation depth, and the measured current and voltage;
    computer readable code for comparing a desired dose rate to the actual dose rate;
    computer readable code for increasing the applied voltage when the actual dose rate is less than the predetermined dose rate; and
    computer readable code for decreasing the applied voltage when the actual dose rate is greater than the predetermined dose rate.

20. A system for emitting x-rays comprising:
    means for measuring current and voltage;
    means for determining an actual dose rate based on an emitter cutoff-energy, a radiation depth, and a measured current and voltage;
    means for comparing a desired dose rate to the actual dose rate; and
    means for matching the actual dose rate to the desired dose rate by increasing and decreasing an applied voltage.

* * * * *